Figure 1:
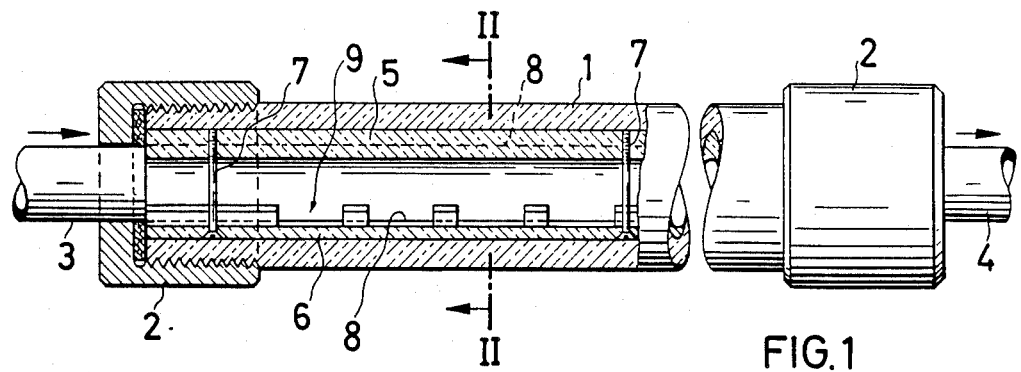

United States Patent [19]

Penina-Surinach

[11] Patent Number: 4,705,754
[45] Date of Patent: Nov. 10, 1987

[54] BIOFOULING SIDE-STREAM APPARATUS (BSSA) FOR MONITORING THE MICROBIAL GROWTH IN OILFIELD WATER SYSTEMS

[75] Inventor: Pere Penina-Surinach, Kelkheim, Fed. Rep. of Germany

[73] Assignee: Hoechst Aktiengesellschaft, Fed. Rep. of Germany

[21] Appl. No.: 897,827

[22] Filed: Aug. 19, 1986

[30] Foreign Application Priority Data

Aug. 21, 1985 [DE] Fed. Rep. of Germany ....... 3529848

[51] Int. Cl.$^4$ .............................................. C12M 1/00
[52] U.S. Cl. ...................................... 435/287; 435/30; 435/299
[58] Field of Search ..................... 435/30, 31, 34, 287, 435/293, 299, 813, 819

[56] References Cited

U.S. PATENT DOCUMENTS 3,301,067  1/1967  Brundage, Jr. ..................... 435/292

OTHER PUBLICATIONS

McCoy et al., "Observations of Fouling Biofilm Formation", Canadian Journal of Microbiology, vol. 27,–910 (1981).

Primary Examiner—Samuel Scott
Assistant Examiner—H. A. Odar
Attorney, Agent, or Firm—Connolly and Hutz

[57] ABSTRACT

The apparatus for continuously monitoring the microbial growth in oilfield water systems comprises a pipe (1) which is made of transparent material and which is sealed at both ends with screw-on caps (2) and is provided in each case with an inlet and outlet line (3, 4), and a plurality of steel sleeves which are held within the pipe at its upper edge by a bar (5) in the longitudinal direction of the pipe and at its lower edge by a rail with a U-shaped cross-section (6), the lower U-shaped rail being provided with recesses for receiving the steel sleeves and the upper bar being kept at a distance from the lower U-shaped rail by bolts (7).

1 Claim, 2 Drawing Figures

U.S. Patent     Nov. 10, 1987     4,705,754

BIOFOULING SIDE-STREAM APPARATUS (BSSA) FOR MONITORING THE MICROBIAL GROWTH IN OILFIELD WATER SYSTEMS

As is known, the conveying of crude oil and secondary recovery systems give rise to problems which are caused by the growth of sulfate-reducing bacteria. The growth of the organic matter results in constrictions in the pipe cross-sections, and the hydrogen sulfide which is formed at the same time leads to corrosion damage to the metallic materials of the oilfield water systems. To avoid this damage, it is necessary to add to the water injection system or water-oil emulsions circulating in these oilfield water systems certain amounts of bactericidally active compounds. It is an object of the present invention to provide suitable apparatuses for continuously monitoring the growth of the microbes so as to be able to add the right amount of biocide at the right time.

The present invention provides a novel apparatus for continuously monitoring the microbial growth in oilfield water systems, this apparatus comprising a pipe (1) which is made of transparent material and which is sealed at both ends with screw-on caps (2) and is provided in each case with an inlet and outlet line (3, 4), and a plurality of steel sleeves which are held within the pipe at its upper edge by a bar (5) in the longitudinal direction of the pipe and at its lower edge by a rail with a U-shaped cross-section (6), the lower U-shaped rail being provided with recesses (9) for receiving the steel sleeves and the upper bar being kept at a distance from the lower U-shaped rail by bolts (7).

Figure 2:
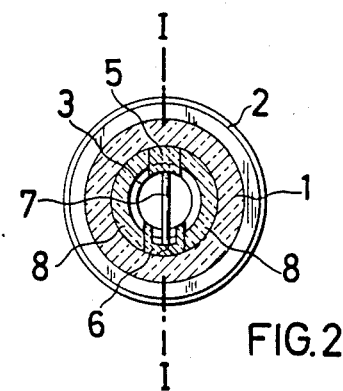

An apparatus of this type is depicted in longitudinal section in FIG. 1 and in cross-section in FIG. 2.

The apparatus comprises a pipe (1) which is made of transparent plastic (Plexiglas ®) and is sealed at both ends by screwed-on metal caps (2). The inlet and outlet pipes (3 and 4) for the water or the oil-water emulsion are guided through these metal caps and can each be blocked off by valves. Within the pipe there is a two-part support system for a comparatively large number of steel sleeves, hereinafter referred to as test coupons. The upper part of this support system (5) is a bar which has an approximately square cross-section and is arranged in the longitudinal direction of the pipe. The lower part of the support system has a U-shaped cross-section, and the side walls of this lower support are shortened at regular intervals. The recesses (9) thus obtained serve for receiving the test coupons, which are not depicted in the Figures. The number of these recesses and hence the number of test coupons should be 10 to 50, in particular 20 to 30. The lower and the upper part of the support system are kept at a distance by bolts (7) in such a way that the entire support system bears lightly against the inner surface of the pipe (1). The test coupons which are fixed within the pipe by means of this support system are short, tubular sections of steel of the type customarily used for determining corrosion.

To narrow the cross-section of the pipe (1), it is possible to insert segment-shaped parts (8) on both sides across the entire length of the pipe. As a result the amount of water flowing through the pipe is reduced. These segment-shaped parts and also the two parts of the support system are likewise composed of Plexiglas.

In a preferred embodiment, the apparatus comprises a Plexiglas pipe having an internal diameter of 2 cm, an external diameter of 3 cm and a length of 35 cm. The upper part of the support system for the test coupons has a height of 5 mm and a width of 6 mm. The lower part of the support system has a width of 8 mm, and the two side walls are each 1.5 mm in thickness. The height of the walls is 5 mm, and to receive the test coupons these walls are shortened sectionally in accordance with the length of the test coupons and in accordance with the number of test coupons to a height of 2 mm. The number of test coupons in the case of this preferred embodiment is 24. The entire apparatus is designed in such a way that it can be operated at temperatures of 0° to 100° C. and pressures of 0 to 10 bar.

The apparatus described is installed for the monitoring of bacterial growth in the side stream at strategically important points of the oilfield water systems to be monitored. These include in particular the point immediately behind the place where the biocide is metered in and also the points located at the remote ends of the system.

It is particularly advantageous to install a plurality of apparatuses of this kind in the oilfield water system, and one apparatus can then be used to monitor the bacterial growth at short intervals, for example at intervals of 1 week, and the other apparatuses can serve for long-term monitoring. It is also possible to connect two or more apparatuses of the type described above in series.

Bacterial growth is monitored by means of this apparatus as follows. First the apparatus is separated off from the system to be monitored by closing the two cocks and is removed. One of the two sealing caps is unscrewed, and the support system with the first test coupons is partly pulled out of the pipe. By moving the two parts of the support system apart the test coupons can easily be removed. The test coupons are dropped into a sterile, sealable vessel, and from there they are transferred by means of forceps to a vessel with nutrient solution, where they are cultivated for developing the bacterial growth. Thereafter the amount of bacteria present can then be determined. All this is done by the methods customary and known in microbiology. In this way it is possible to determine whether and to what extent the test coupons are infected with bacterial growth. At the same time this then also indicates the extent of bacterial growth in the parallel part of the system to be monitored. By adding different bactericides in different amounts to each unit of an assembly in series connected to a given point of the oilfield water system, it is readily possible in this way to monitor the bacterial growth, and the optimal conditions for preventing bacterial growth can be established for every case. By fitting a plurality of apparatuses of the type described it is possible, as described above, to monitor bacterial growth at different intervals. As a result of the fact that the external pipe of the apparatus comprises a transparent material it is even possible to check the test coupons purely visually for corrosive deposits due to bacterial growth.

I claim:

1. Biofouling side-stream apparatus for continuously monitoring microbial growth in oilfield water systems comprising a pipe of transparent material, screw-on caps, one at each end of the pipe sealingly connected to the pipe, each end cap having an opening therein, an inlet line extending through one of the cap openings and an outlet line extending through the other cap opening, and a plurality of steel sleeves held within the pipe at its upper edge by a bar in the longitudinal direction of the pipe and at its lower edge by a rail having a U-shaped cross-section, the lower U-shaped rail including recesses for receiving the steel sleeves, and means spacing the upper bar at a distance from the lower U-shaped rail.

* * * * *